United States Patent
Ferree

(10) Patent No.: US 6,878,167 B2
(45) Date of Patent: Apr. 12, 2005

(54) METHODS AND APPARATUS FOR PLACING INTRADISCAL DEVICES

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/421,434

(22) Filed: Apr. 23, 2003

(65) Prior Publication Data

US 2004/0024459 A1 Feb. 5, 2004

Related U.S. Application Data

(60) Provisional application No. 60/375,185, filed on Apr. 24, 2002, and provisional application No. 60/378,132, filed on May 15, 2002.

(51) Int. Cl.[7] .................................................. A61F 2/44
(52) U.S. Cl. .................................................... 623/17.16
(58) Field of Search .................... 606/60–64; 623/17.16

(56) References Cited

U.S. PATENT DOCUMENTS

| 5,556,431 A | * | 9/1996 | Buttner-Janz | 623/17.15 |
| 6,001,130 A | * | 12/1999 | Bryan et al. | 623/17.16 |
| 6,494,883 B1 | * | 12/2002 | Ferree | 606/61 |
| 6,558,423 B1 | * | 5/2003 | Michelson | 623/17.11 |
| 6,652,585 B2 | * | 11/2003 | Lange | 623/17.11 |

* cited by examiner

Primary Examiner—Glenn K. Dawson
Assistant Examiner—D. Jacob Davis
(74) Attorney, Agent, or Firm—Gifford, Krass, Groh, Sprinkle, Anderson & Citkowski, PC

(57) ABSTRACT

An osteotomy of a portion of a vertebral endplate and/or vertebral body allows for easier insertion of a device that fits tightly into a disc space. A different aspect of the invention resides in a mechanical device to hold the osteotomized portion of the vertebra against the vertebral body after the intradiscal device is placed. The device may be removed after the pieces of vertebra heal and fuse together.

6 Claims, 19 Drawing Sheets

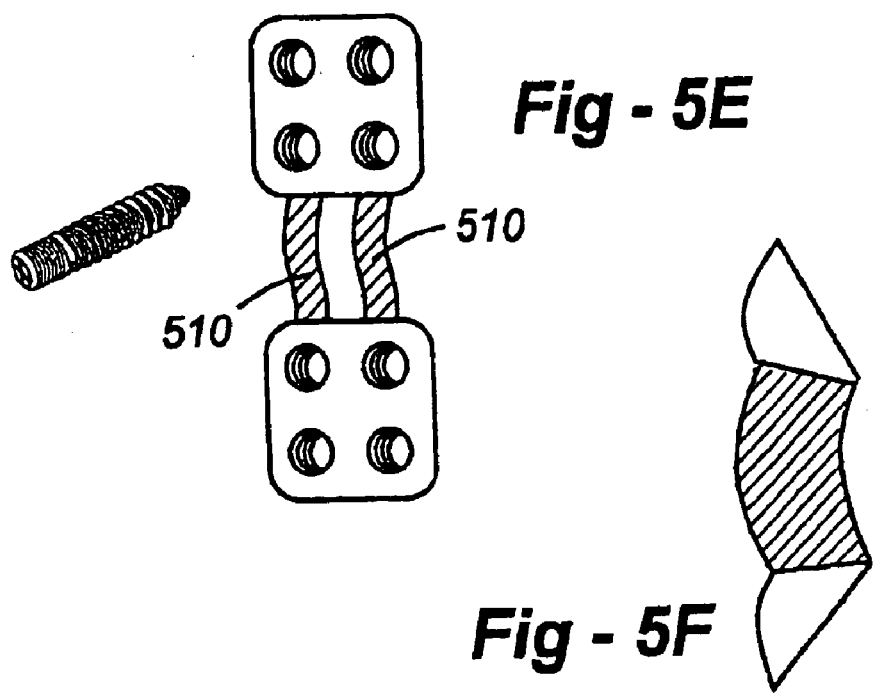
Fig - 5E
Fig - 5F
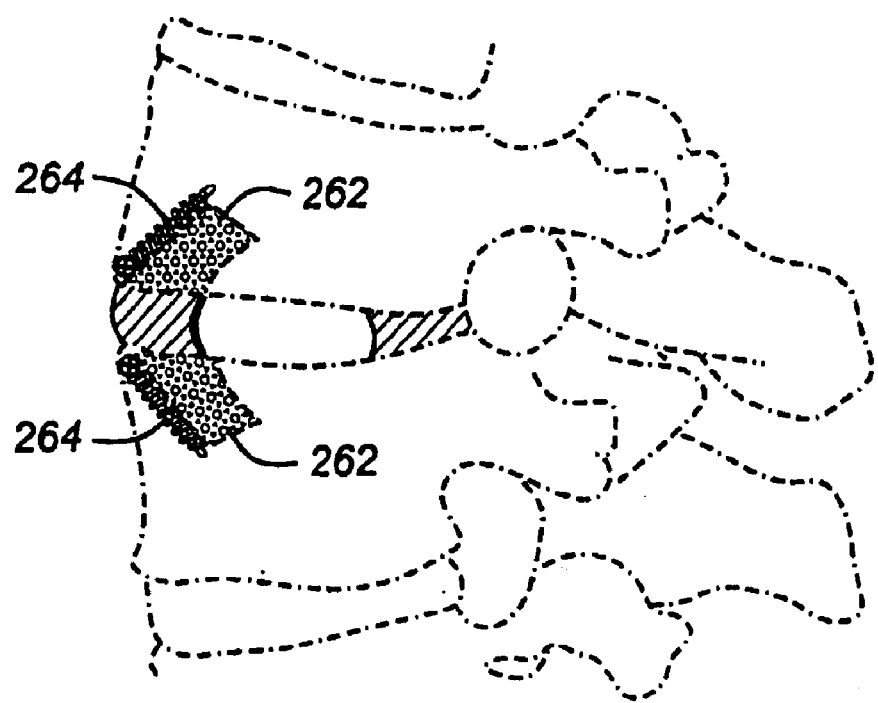
Fig - 5G

METHODS AND APPARATUS FOR PLACING INTRADISCAL DEVICES

REFERENCE TO RELATED APPLICATIONS

This application claims priority from U.S. Provisional Patent Application Ser. Nos. 60/375,185, filed Apr. 24, 2002 and 60/378,132, filed May 15, 2002; the entire content of each being incorporated herein by reference.

FIELD OF THE INVENTION

This invention relates generally to spinal surgery and, in particular, to methods and apparatus for placing intradiscal devices.

BACKGROUND OF THE INVENTION

Intradiscal devices are often shaped to fit within the natural concavities of the vertebral endplates that make up the disc space. As shown in FIG. 1, the entrance into the disc space is often narrower than the vertical space within the disc space. Currently surgeons have three choices when inserting devices that fit tight within the interior of the natural disc space. First, they can insert devices that change size or shape within the disc space. There are only a limited number of intradiscal devices that change size or shape within the disc space. Second, surgeons can remove a portion of the vertebrae endplate to allow the insertion of a device that fits tightly in the tallest portion of the disc space. Third, surgeons can distract the vertebrae to insert the intradiscal device. However, at times, the vertebrae cannot be distracted enough to allow the insertion of an intradiscal device that fits tightly within the central portion of the disc space and yet can be inserted past the periphery of the disc space.

SUMMARY OF THE INVENTION

The present invention involves an osteotomy of a portion of a vertebral endplate and/or vertebral body to allow for easier insertion of a device that fits tightly into a disc space, especially the tallest portion(s) of the disc space. A different aspect of the invention resides in a mechanical device to hold the osteotomized portion of the vertebra against the vertebral body after the intradiscal device is placed. The device may be removed after the pieces of vertebra heal and fuse together.

BRIEF DESCRIPTION OF THE DRAWINGS

FIG. 5E is an exploded view of the front of the plates and a screw shown in FIG. 5D;

FIG. 5F is a view of the side of bone and AF graft shown in FIG. 5C;

FIG. 5G is a sagittal cross section of an alternative embodiment;

DETAILED DESCRIPTION OF THE INVENTION

Figure 1:
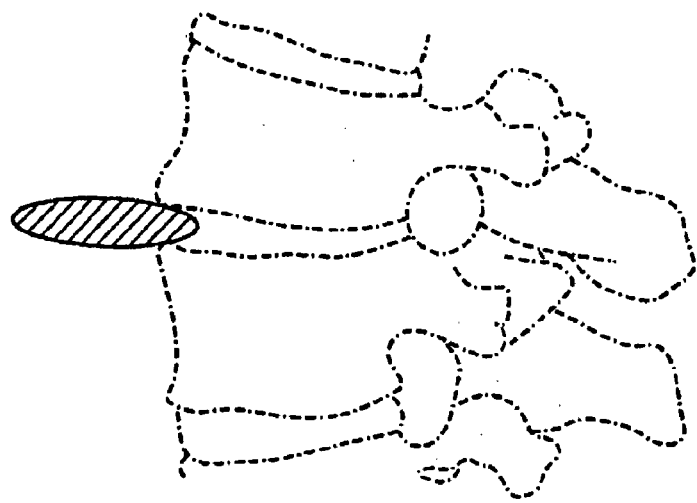
FIG. 1 shows a prior art device illustrating the entrance into the disc space.
Figure 2A:
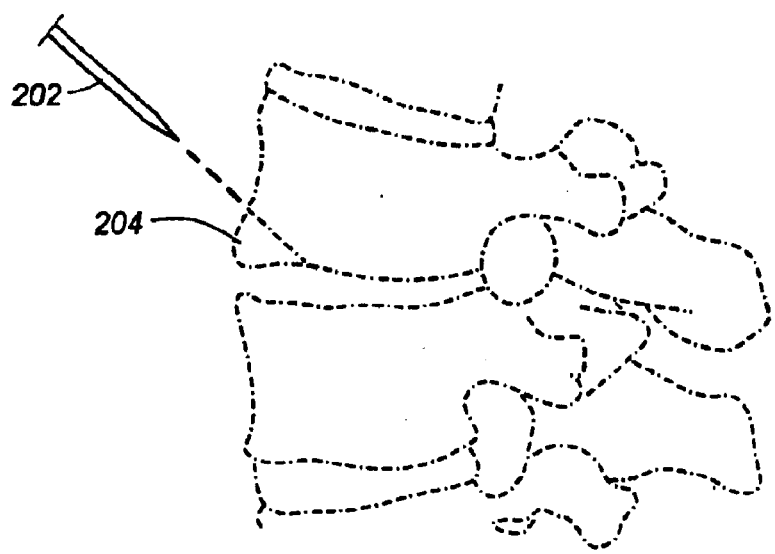
FIG. 2A is a side-view drawing illustrating an approach taken according to a method of the present invention.
Figure 2B:
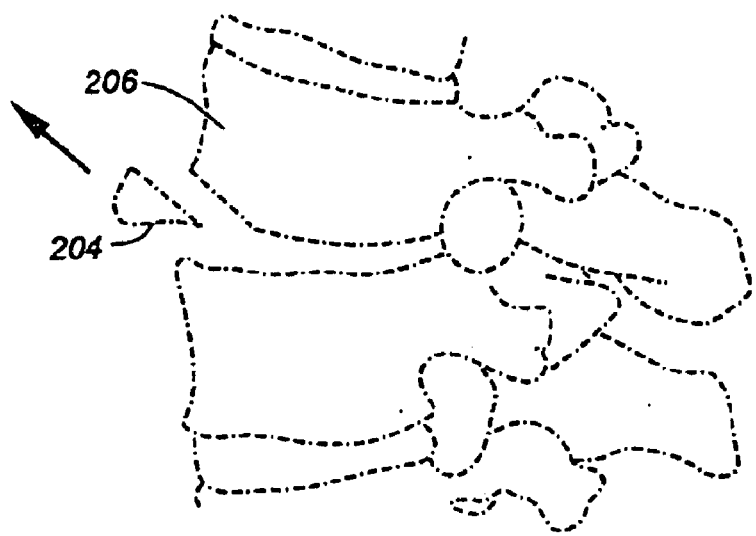
FIG. 2B shows a portion removed from the vertebrae.
Figure 2C:
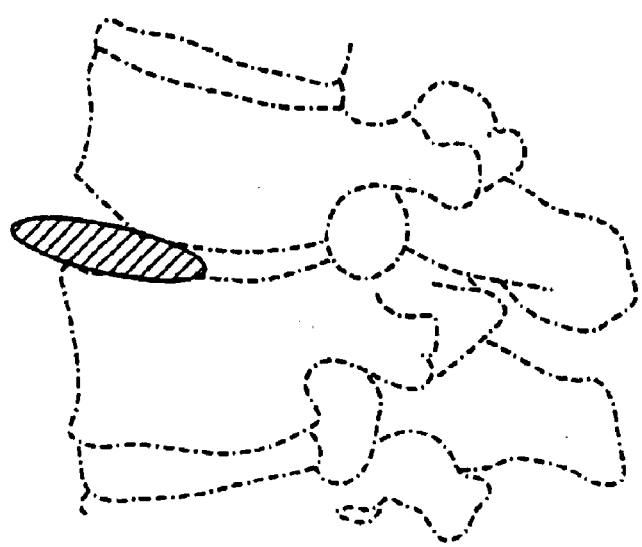
FIG. 2C shows how, with the portion removed, the intradiscal device may be more easily inserted.
Figure 2D:
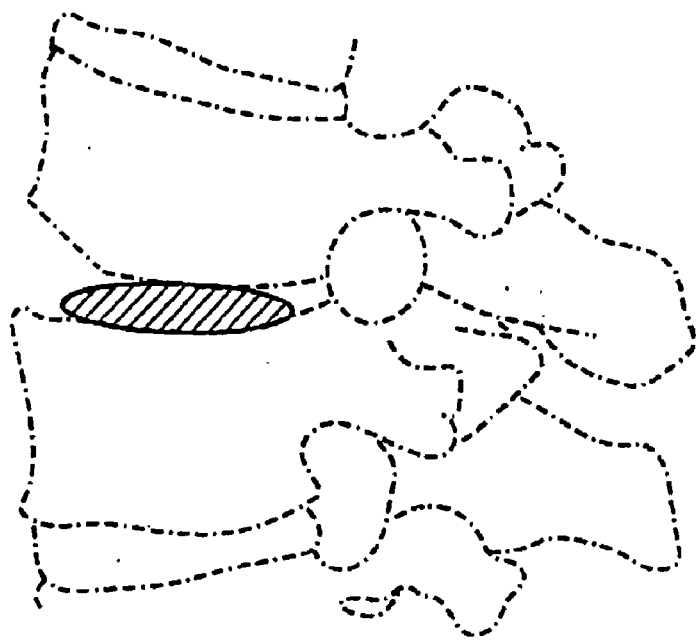
FIG. 2D shows the intradiscal device in place in an intervertebral space.
Figure 2E:
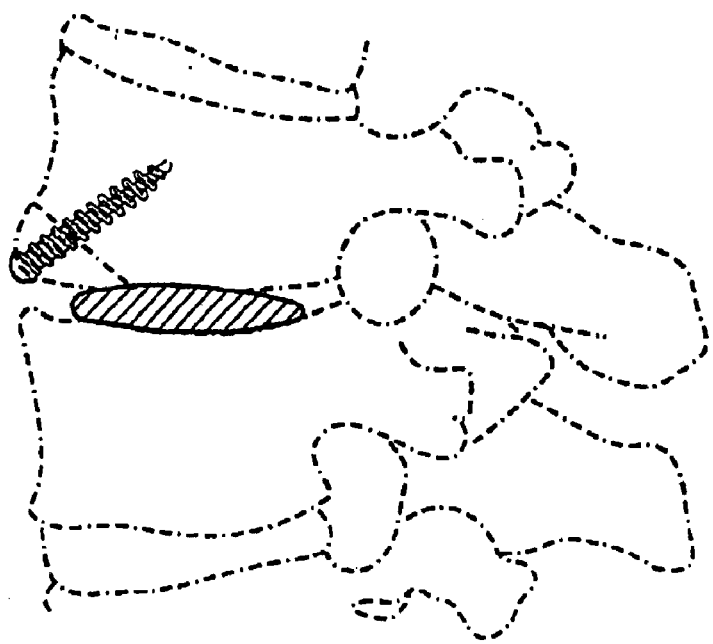
FIG. 2E shows the replacement of an osteotomized portion.

FIG. 2A is a side-view drawing illustrating an approach taken according to a method of the invention. In particular, a tool such as an osteotome 202 is used to remove or truncate a lower anterior portion of the upper vertebrae 206. FIG. 2B shows the portion removed from the vertebrae. FIG. 2C shows how, with the portion removed, the intradiscal device may be more easily inserted. FIG. 2D shows the intradiscal device in place in the intervertebral space. FIG. 2E shows the replacement of the osteotomized portion. Note that the piece of bone itself may be drilled and/or tapped if necessary, preferably before the osteotomy, to assist with reattachment.

Figure 2F:
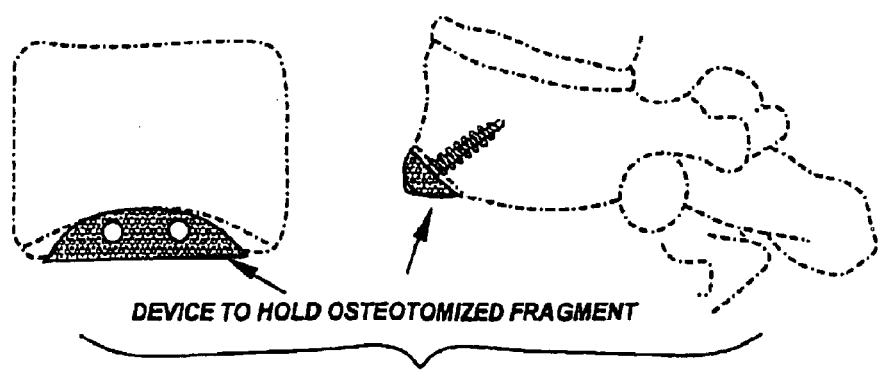
FIG. 2F shows anterior and lateral views illustrating a device is used to hold the osteotomized fragment.
Figure 2G:
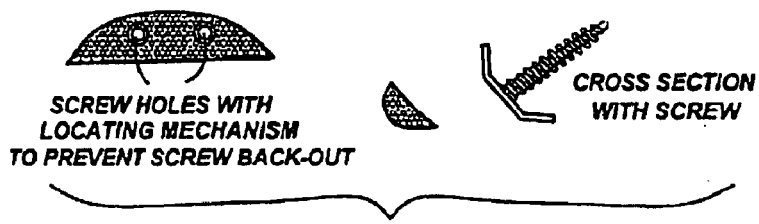
FIG. 2G shows anterior and lateral views of a fragment-holding device with the lateral or side view being shown in cross-section.
Figure 3A:
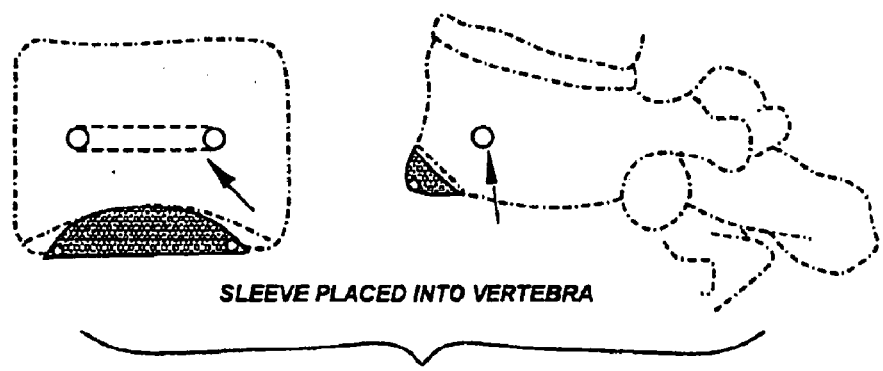
FIG. 3A shows an anterior and lateral view of a hole formed through the vertebrae to receive a cable.
Figure 3B:
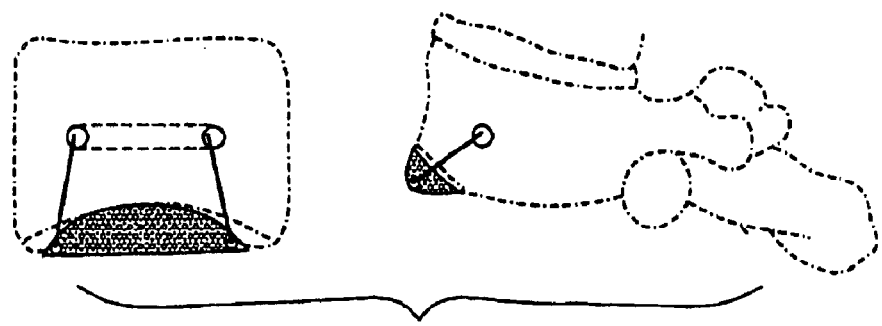
FIG. 3B is a drawing which shows the holder in place and secured with the cable.

FIG. 2F provides an anterior and lateral view showing the way in which the device is used to hold the osteotomized fragment. FIG. 2G is an anterior and lateral view of the preferred fragment-holding device, with the lateral or side view being shown in cross-section. As an alternative to a plate and fasteners, a cable system may be used to hold the osteotomized portion in place. FIG. 3A shows an anterior and lateral view of a hole formed through the vertebrae to receive a cable, and FIG. 3B is a drawing which shows the holder in place and secured with the cable.

It will be appreciated, that although, in the preferred embodiment, only a portion of the upper vertebrae is osteotomized, an anterior portion of the lower vertebrae or both the upper and lower vertebrae may be modified according to the invention, depending upon the area of the spine, patient's physiology and other factors. Indeed, if both the upper and lower vertebrae are osteotomized, the angle of approach may be reduced.

Additionally, the anterior, lateral, and/or posterior portions of the vertebrae may be osteotomized according to the invention, and the osteotomized bone fragment(s) may include attached Annulus Fibrosus (AF). Although the osteotomy may be limited to either the vertebra above or below the disc, alternatively osteotomies can be performed on the vertebra above and below the disc. An allograft bone and AF component, or an allograft bone and tendon/ligament component, may be used to reconstruct the AF.

Figure 4A:
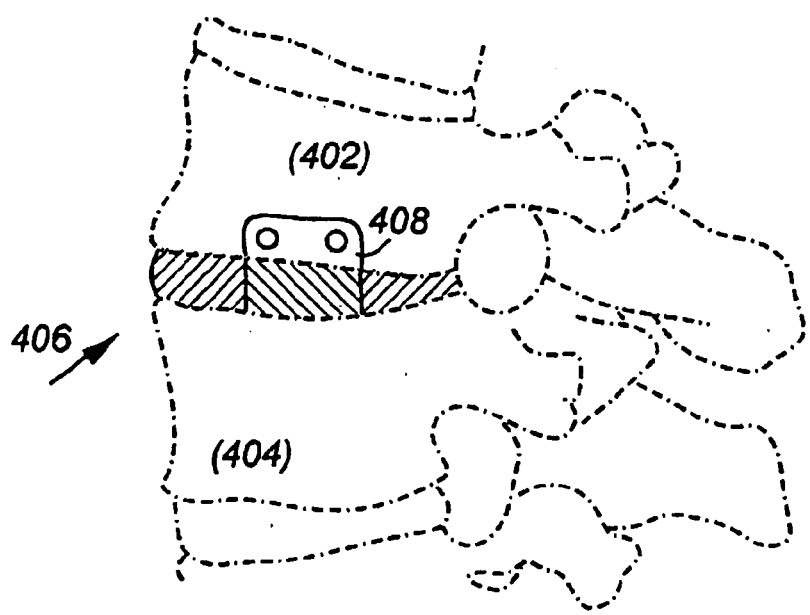
FIG. 4A is a view of the lateral surface of two vertebrae, a disc, and an osteotomized piece of vertebra.
Figure 9A:
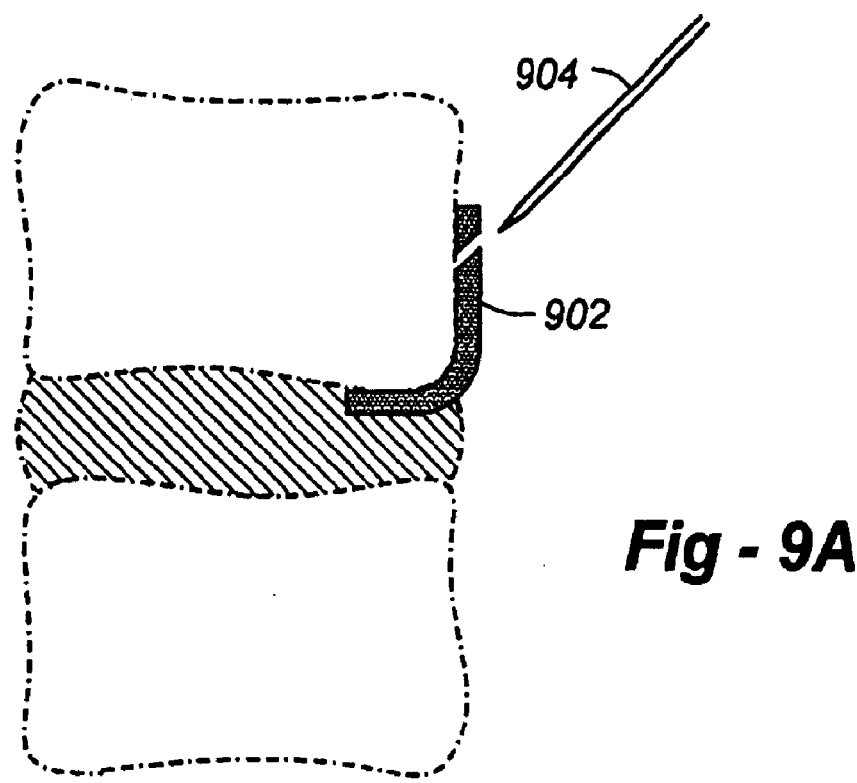
FIG. 9A is a coronal cross section of the spine, a drill and osteotomy guide, and an osteotome.
Figure 9B:
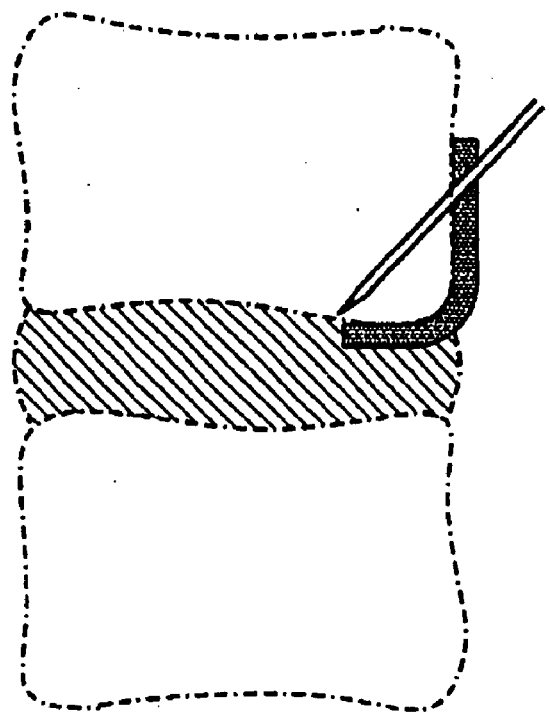
FIG. 9B is a coronal cross section of the spine and the embodiment of the invention shown in FIG. 9A.

FIG. 4A is a view of the lateral surface of two vertebrae 402, 404, a disc 406, and an osteotomized piece of vertebra 408. The dotted area of the drawing represents the osteotomized bone fragment. The bone fragment and vertebra can be drilled and tapped prior to the osteotomy. A guide as shown in FIGS. 9A and 9B can be used to drill, tap, and cut the vertebra. The Annulus Fibrosus (AF, 410) is cut.

Figure 4B:
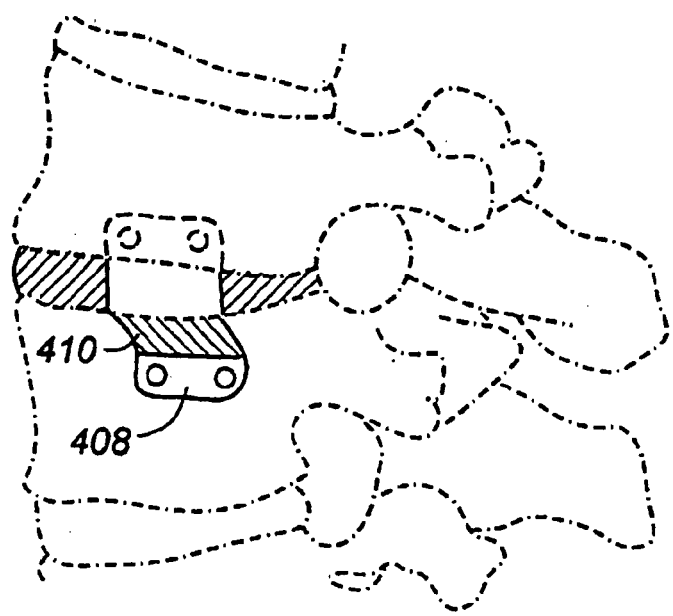
FIG. 4B is a is a view of the lateral surface of the spine with the osteotomized bone fragment and the attached AF retracted inferiorly.

A portion of the AF that is attached to the bone fragment is separated from the remainder of the AF. FIG. 4B is a view of the lateral surface of the spine with the osteotomized bone fragment 408 and the attached AF 410 retracted inferiorly, to allow entry into the disc space. The area outlined by the dotted lines in the superior vertebra represents the cut surface of the superior vertebra.

Figure 4C:
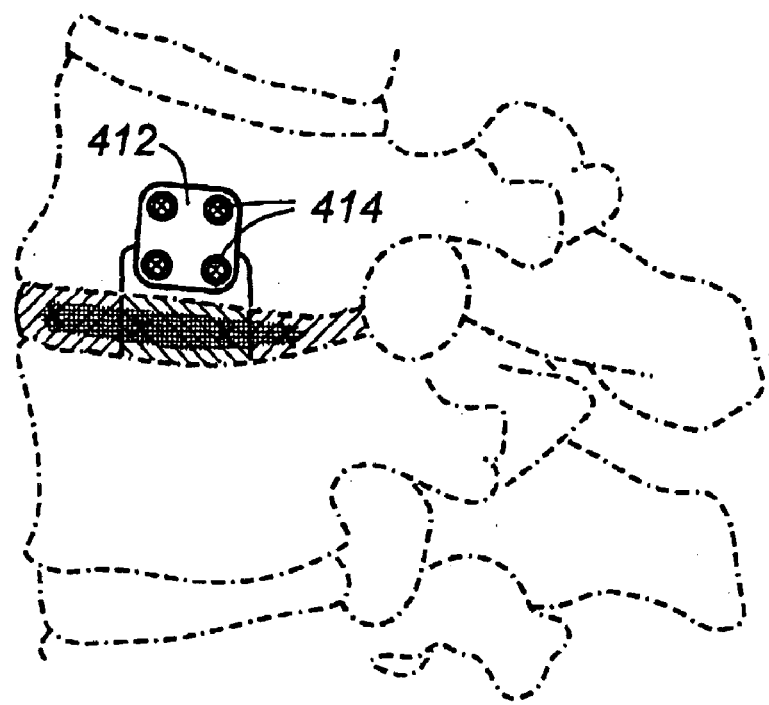
FIG. 4C is a view of the lateral surface of the spine after reattaching the osteotomized bone fragment.

FIG. 4C is a view of the lateral surface of the spine after reattaching the osteotomized bone fragment. A plate 412 and screws 414 can be used to hold the bone fragment in position. The plate in this case is limited to a single vertebra (area of the drawing with horizontal lines), and does not project beyond the vertebral. endplate. The plate may further include a mechanism that prevents the screws from backing out of the plate. For example, C-rings that snap shut after the screws pass by the C-rings can be incorporated into the plate. The screws can pass through the bone fragment and/or portion of the vertebra above the fragment.

Figure 4D:
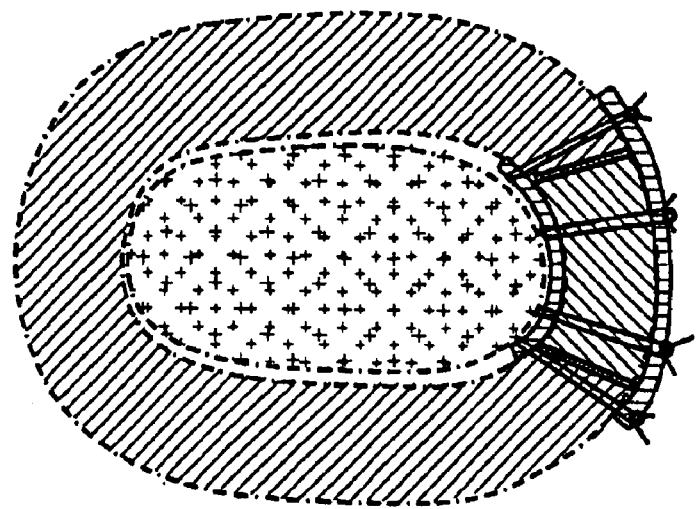
FIG. 4D is an axial cross-section of a disc, an intradiscal device and attached mesh.

FIG. 4C shows screws passing through the bone fragment and screws that do not pass through the bone fragment. Mesh, as described in my U.S. Pat. No. 6,371,990 is shown attached to the cut and uncut portions of the AF. The mesh is represented by the portion of the drawing with vertical and horizontal lines. FIG. 4D is an axial cross section of a disc, an intradiscal device, and the attached mesh. The intradiscal device is represented by the dotted area of the drawing. Pieces of mesh (area of the drawing with horizontal lines) are shown on the inner and outer surfaces of the AF. Sutures pass through both pieces of mesh and the interposed AF.

Figure 4E:
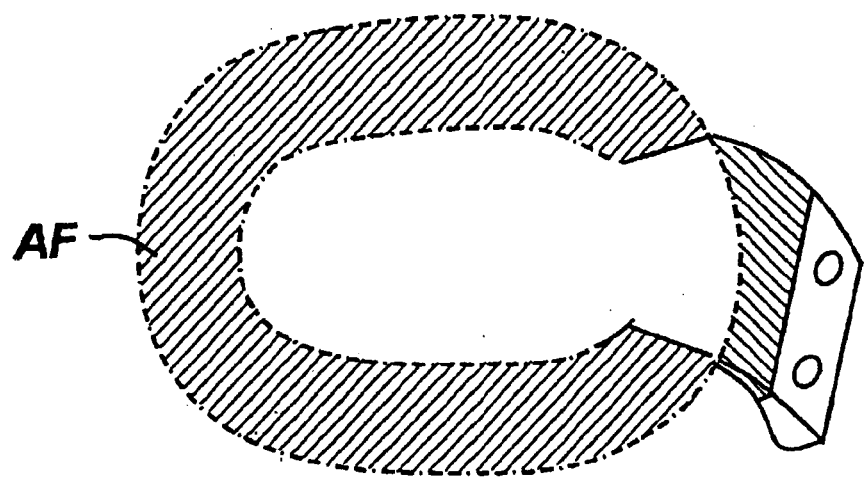
FIG. 4E is an axial cross-section of a disc wherein a bone fragment and attached AF have been retracted.
Figure 4F:
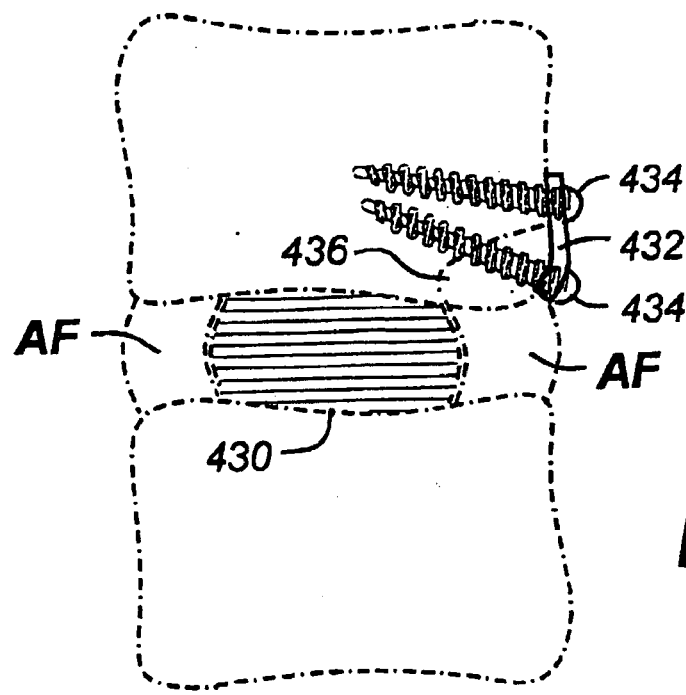
FIG. 4F is a coronal cross-section of the spine, an intradiscal device, and a plate and screws.

FIG. 4E is an axial cross section of a disc wherein a bone fragment and attached AF have been retracted to allow entry into the disc space. FIG. 4F is a coronal cross section of the spine, an intradiscal device 430, and the plate and screws 432, 434 used to hold the bone fragment 436 in position.

Figure 5A:
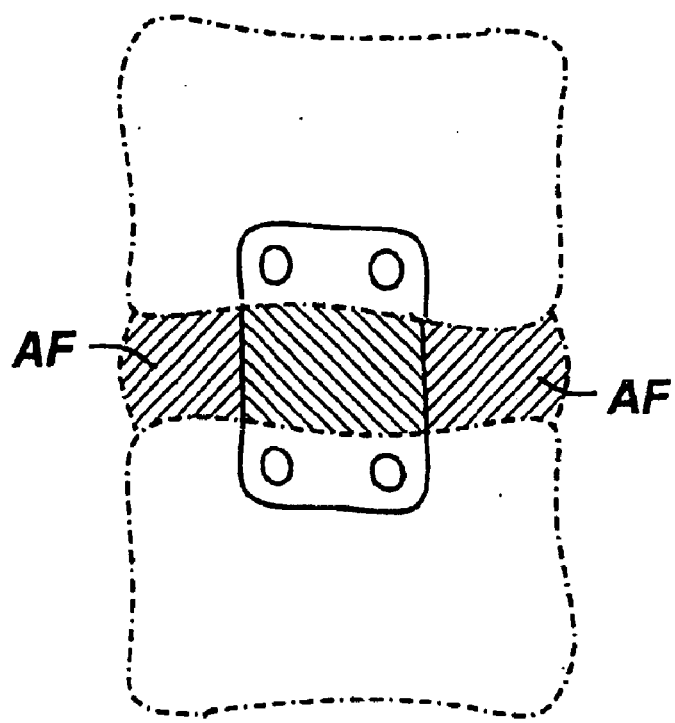
FIG. 5A shows the view of the front of the spine and an alternative embodiment of the invention.
Figure 5B:
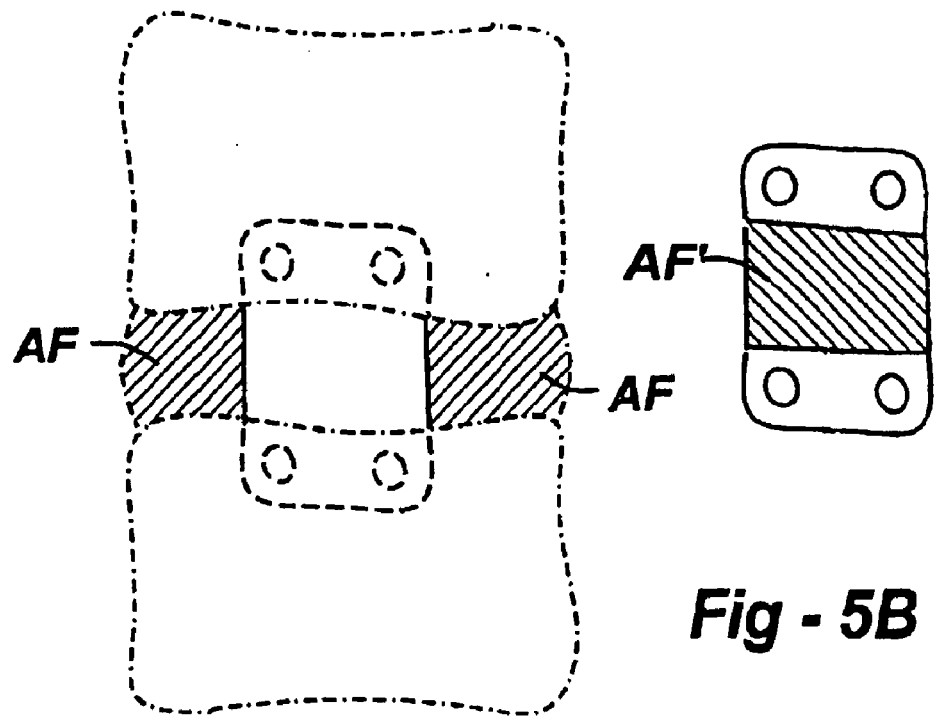
FIG. 5B is a view of the anterior aspect of the spine after removal of the bone fragments.

FIG. 5A is the view of the front of the spine and an alternative embodiment of the invention wherein the vertebrae above and below the disc are osteotomized. A portion of the AF (AF'), attached to both bone fragments, is separated from the remaining AF. FIG. 5B is a view of the anterior aspect of the spine after removal of the bone fragments and the portion of the AF that connects the bone fragments. The separated bone fragments and the AF that connects the bone fragments are on the right side of the drawing.

Figure 5C:
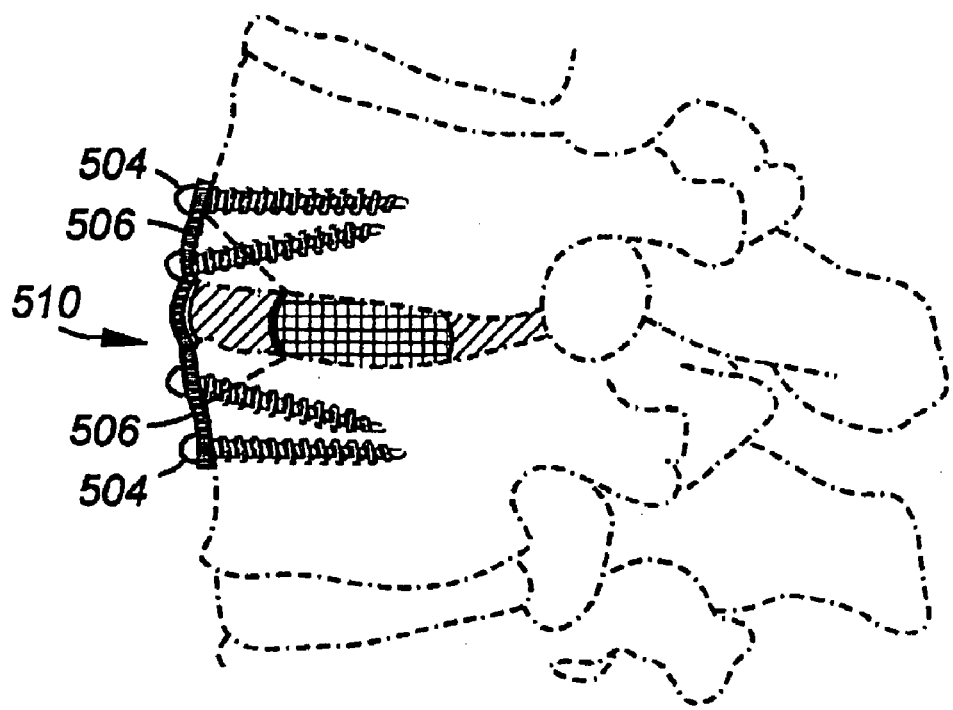
FIG. 5C is a sagittal cross section of the spine, an intradiscal device, and an alternative embodiment of the plate and screws.
Figure 5D:
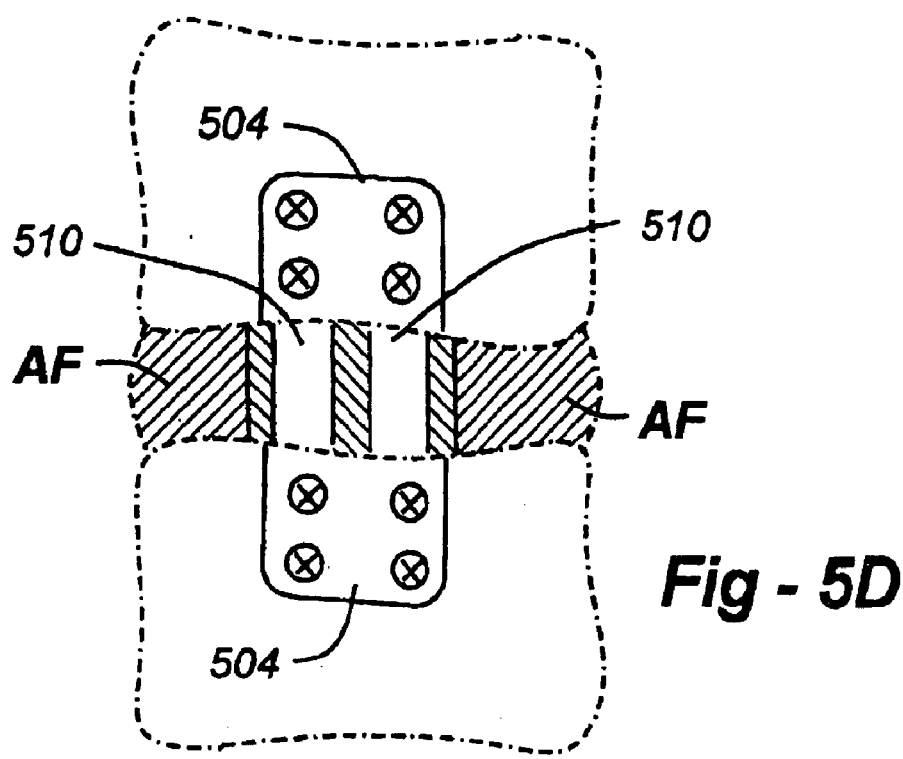
FIG. 5D is a view of the anterior aspect of the spine and the embodiment of the invention shown in FIG. 5C.

FIG. 5C is a sagittal cross section of the spine, an intradiscal device 502, and an alternative embodiment of the plate and screws 504, 506. A flexible material 510 preferably connects the plates. The screws may converge or diverge to increase pull-out strength. FIG. 5D is a view of the anterior aspect of the spine and the embodiment of the invention drawn in FIG. 5C.

FIG. 5E is an exploded view of the front of the plates and a screw drawn in FIG. 5D. The screws can be threaded into the plates, which helps prevent the screws from backing out of the vertebrae. Two or more threads can be used in the portion of the screw that attaches to the plate. The flexible material is shown at 510. FIG. 5F is a view of the side of bone and AF graft drawn in FIG. 5C. The graft may be an autograft or an allograft.

FIG. 5G is a sagittal cross section of an alternative embodiment of the bone and AF graft 262. The graft 262 is preferably held into holes drilled into the vertebrae by interference screws 264. The graft can be autograft or allograft. Allografts could be made from tissues other than vertebrae and AF. For example, the graft could be made of bone from the patella and the tibia with patellar tendon connecting the pieces of bone.

Figure 6A:
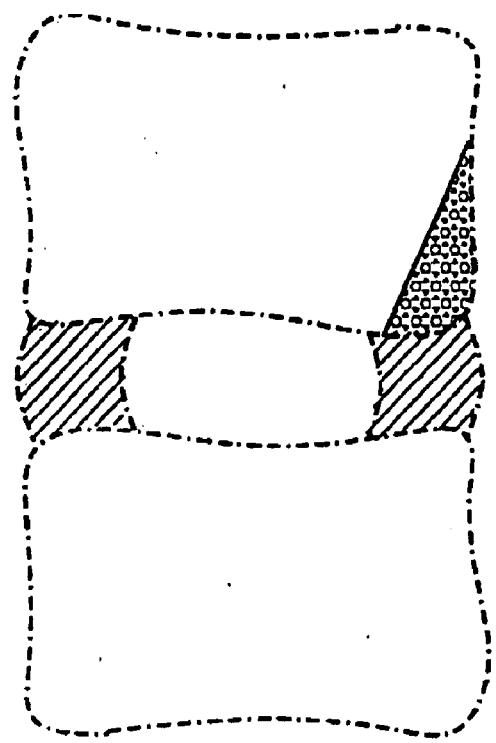
FIG. 6A is a coronal cross-section of the spine, wherein a portion of the upper vertebrae has been osteotomized.
Figure 6B:
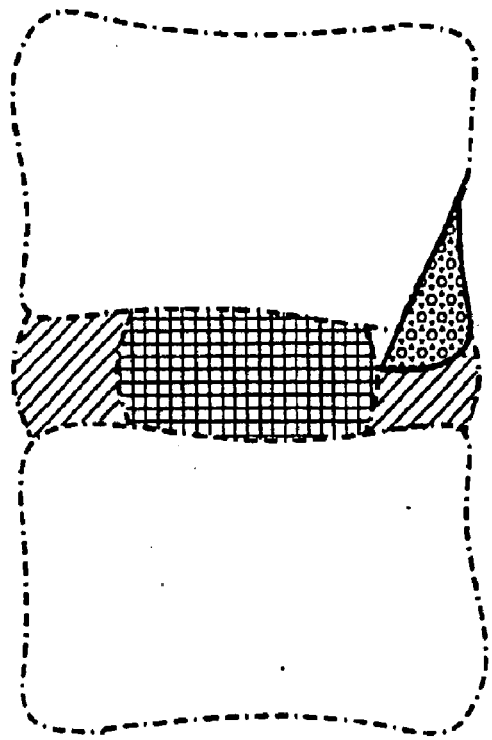
FIG. 6B is a coronal cross-section of the spine shown in FIG. 6A.

FIG. 6A is a coronal cross section of the spine wherein portion of the upper vertebrae has been osteotomized. FIG. 6B is a coronal cross section of the spine drawn in FIG. 6A, after inserting an intradiscal device. The invention allows distraction of the disc space to insert the intradiscal device. The bone fragment can be advanced along the side of the vertebra, after distraction of the disc space.

Figure 7A:
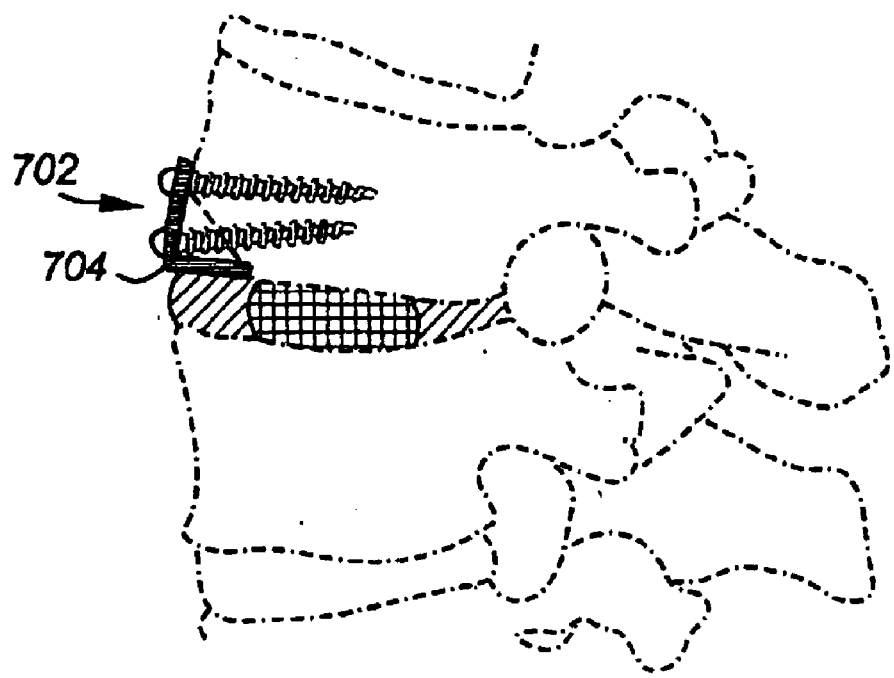
FIG. 7A is a sagittal cross section of the spine, an intradiscal device, and an alterative embodiment of the plate used to attach the bone fragment.
Figure 7B:
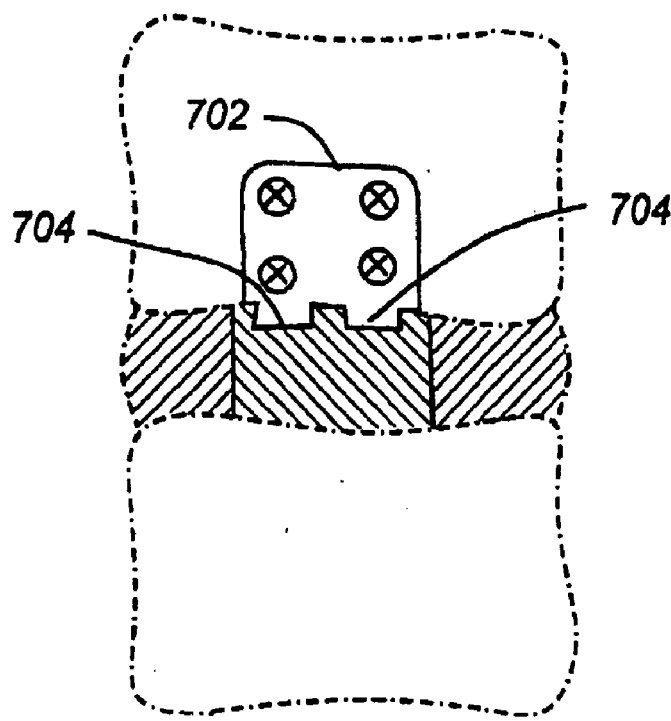
FIG. 7B is a view of the anterior aspect of the spine and the embodiment of the plate shown in FIG. 7A.

FIG. 7A is a sagittal cross section of the spine, an intradiscal device, and an alterative embodiment of the plate 702 used to attach the bone fragment. One or more arms 704 from the bottom of the plate extend under the bone fragment. The arms of the plate also extend through a portion of the AF. FIG. 7B is a view of the anterior aspect of the spine and the embodiment of the plate drawn in FIG. 7A.

Figure 8A:
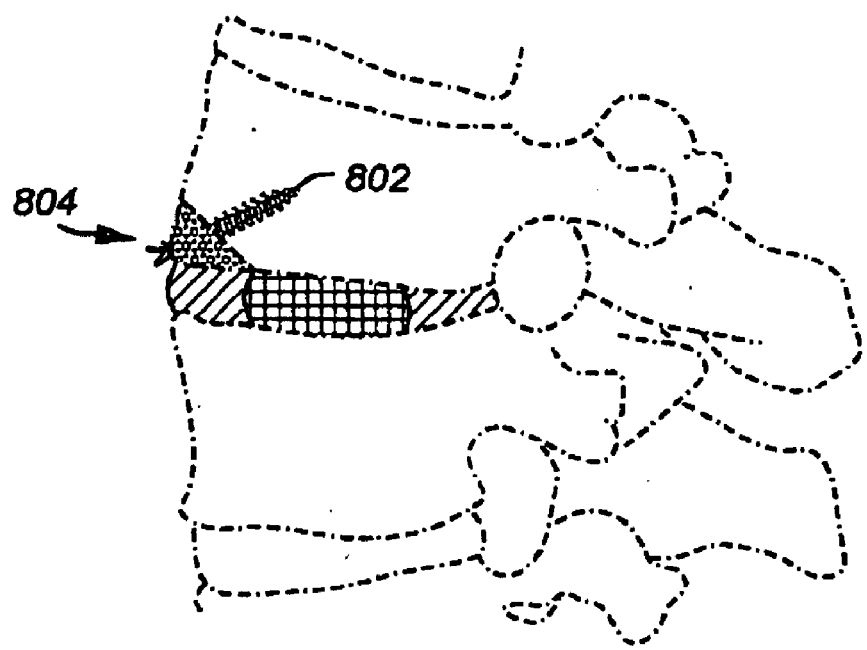
FIG. 8A is a sagittal cross section through the spine and an alternative mechanism used to attach the bone fragment.

FIG. 8A is a sagittal cross section through the spine and an alternative mechanism used to attach the bone fragment. The mechanism includes a screw with member 802 that is threaded into the vertebra and a second component 804 that extends through one or more holes in the bone fragment connects the bone fragment to the vertebra. The drawing illustrates the use of a flexible, suture or cable like component that is tightened over the bone fragment. A nut that threads to a threaded projection through the bone fragment could also be used to attach the bone fragment.

Figure 8B:
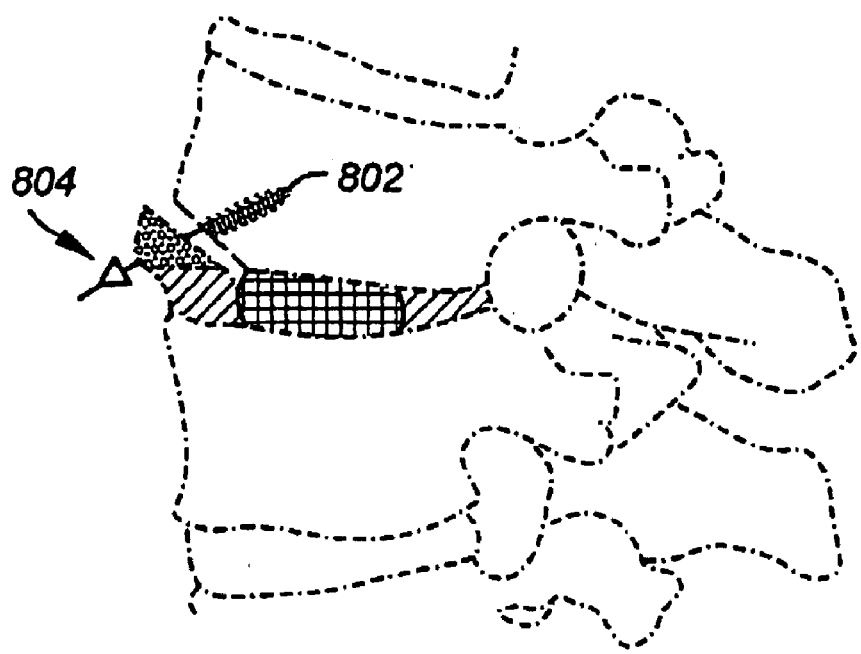
FIG. 8B is a sagittal cross section of the spine and an alternative embodiment of the fastening method shown in FIG. 8A.

FIG. 8B is a sagittal cross section of the spine and an alternative embodiment of the fastening method drawn in FIG. 8A. The fastener may be crimped to a cable extending through the bone fragment, after the bone fragment is placed against the vertebra.

Figure 9C:
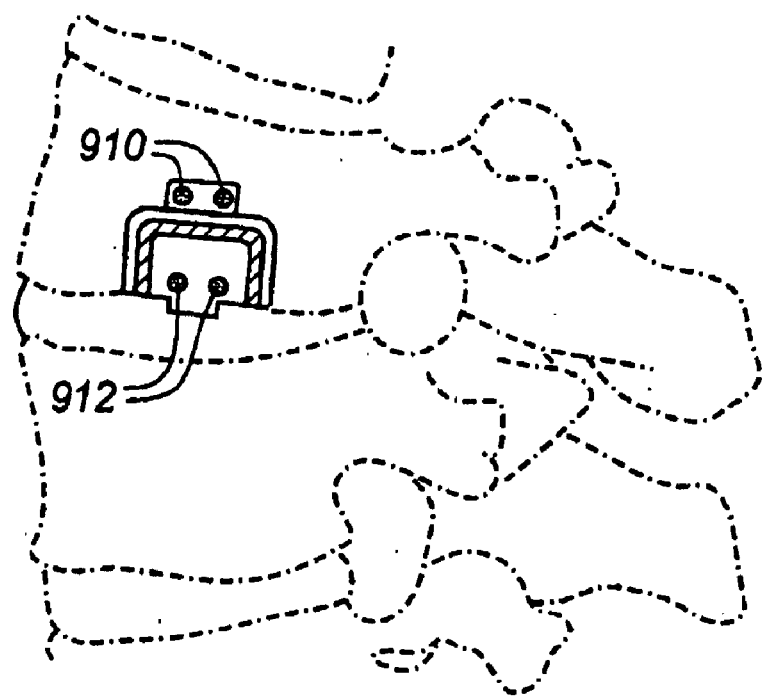
FIG. 9C is a view of the lateral side of the spine and the guide shown in FIG. 9A.
Figure 9D:
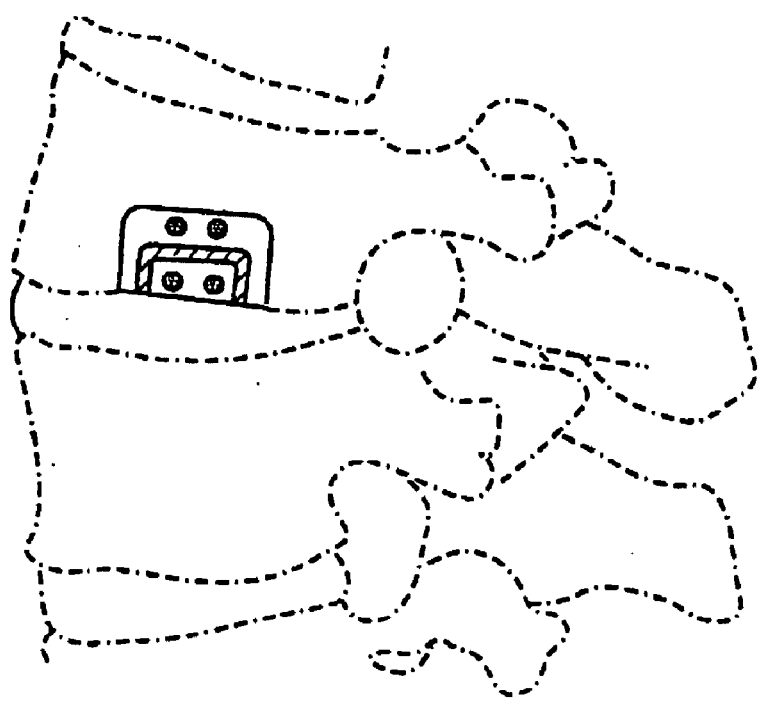
FIG. 9D is a view of the lateral side of the spine and an alternative embodiment of a cutting guide.

FIG. 9A is a coronal cross section of the spine, a drill and osteotomy guide 902, and an osteotome 904. FIG. 9B is a coronal cross section of the spine and the embodiment of the invention drawn in FIG. 9A. The osteotome is drawn extending through the guide and into the vertebra. The guide can also be used to pre-drill and pre-tap holes 910, 912 in the vertebrae and/or the bone fragment. FIG. 9C is a view of the lateral side of the spine and the guide drawn in FIG. 9A. The dotted area of the drawing represents holes in the guide for drilling and tapping the vertebra. The area of the drawing with closely spaced diagonal lines represents the slot for inserting an instrument to cut the vertebra. FIG. 9D is a view of the lateral side of the spine and an alternative embodiment of the cutting guide. The guide drawn in FIG. 9D does not have a component that extends into the disc space. The guide can be held against the vertebra by pins, screws, or taps placed through the holes in the guide.

Figure 10A:
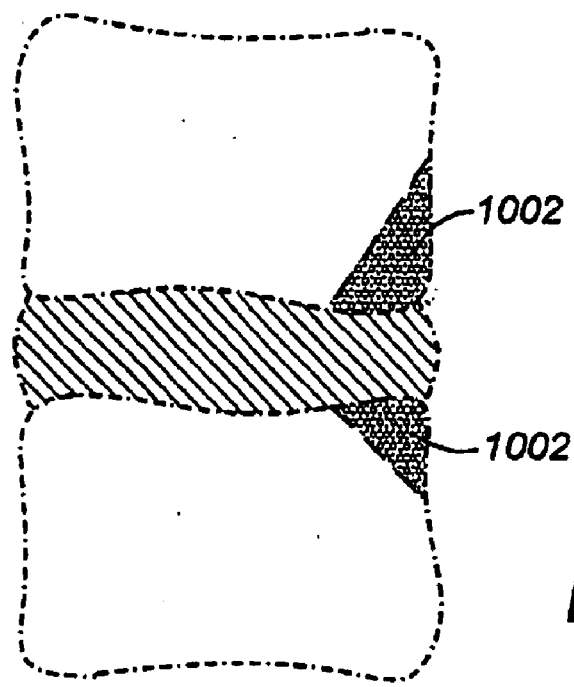
FIG. 10A is a coronal cross section of the spine and an embodiment of the invention with bone fragments having an alternative shape.
Figure 10B:
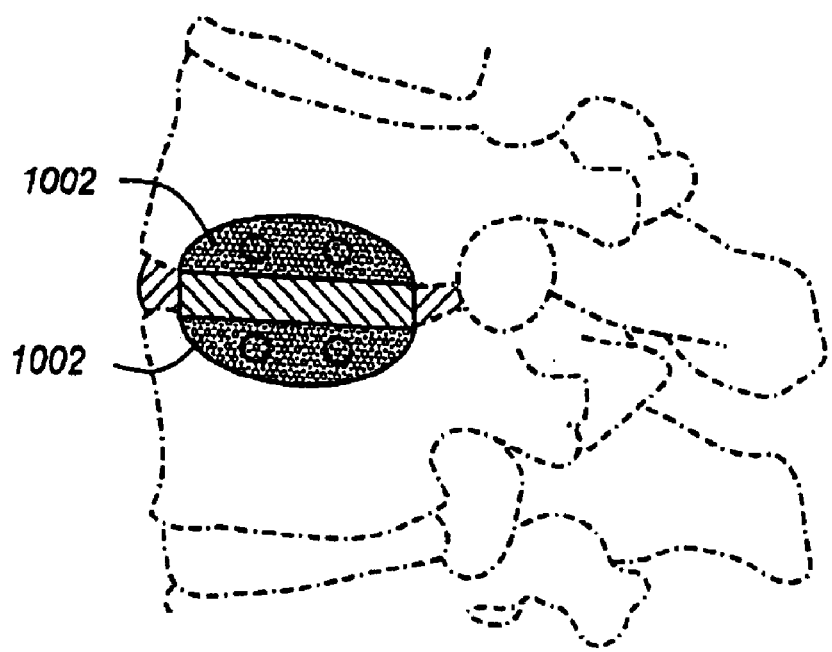
FIG. 10B is a view of the lateral aspect of the spine shown in FIG. 10A.

FIG. 10A is a coronal cross section of the spine and an embodiment of the invention with bone fragments 1002 having an alternative shape. The bone fragments area represented by the dotted area of the drawing. FIG. 10B is a view of the lateral aspect of the spine drawn in FIG. 10A.

Figure 11A:
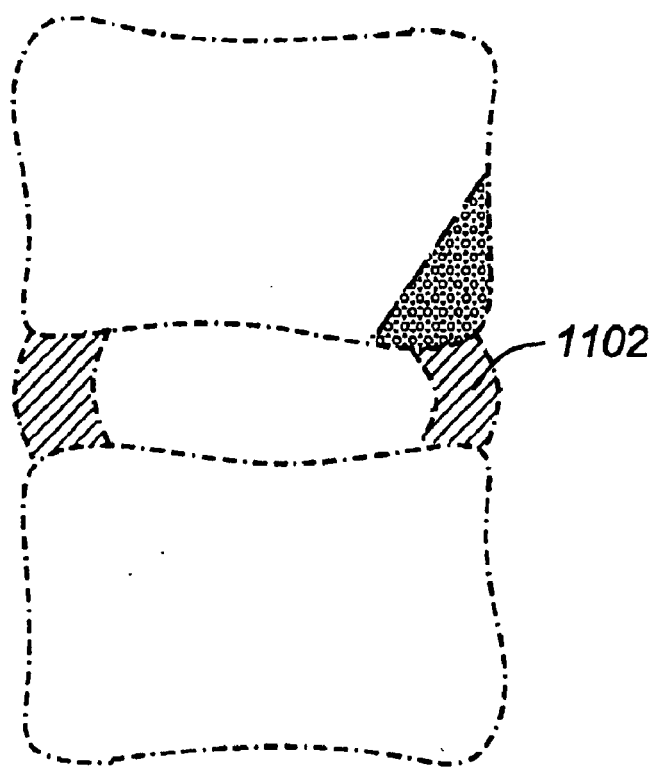
FIG. 11A is a coronal cross section of the spine.
Figure 11B:
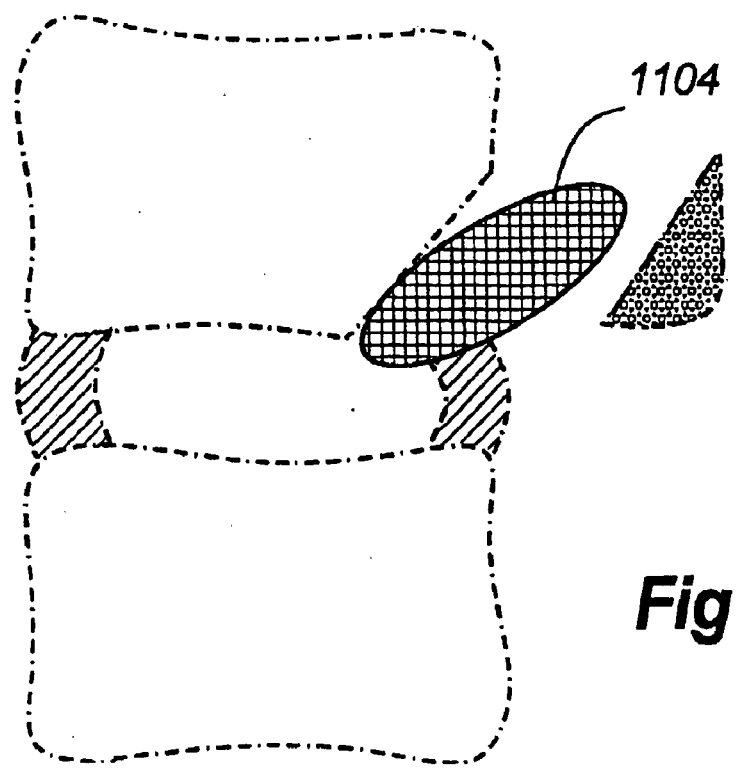
FIG. 11B is a coronal cross section of the spine drawn during the insertion of an intradiscal device.

FIG. 11A is a coronal cross section of the spine. The AF is shown at 1102. The osteotomy extends inside the AF ring. FIG. 11B is a coronal cross section of the spine drawn during the insertion of an intradiscal device. The bone fragment has been removed from the vertebra. The intradiscal device 1104 is inserted into the AF ring. A portion of the nucleus pulposus may be removed to allow room for the intradiscal device. The AF is not cut. The bone fragment may also remain attached to the AF.

Figure 11C:
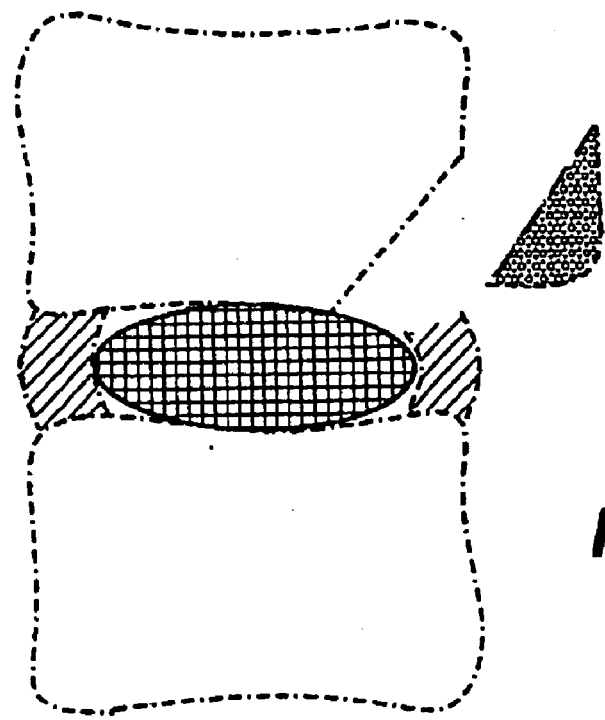
FIG. 11C is a coronal cross section of the spine drawn in FIG. 11B, after the insertion of an intradiscal device.
Figure 11D:
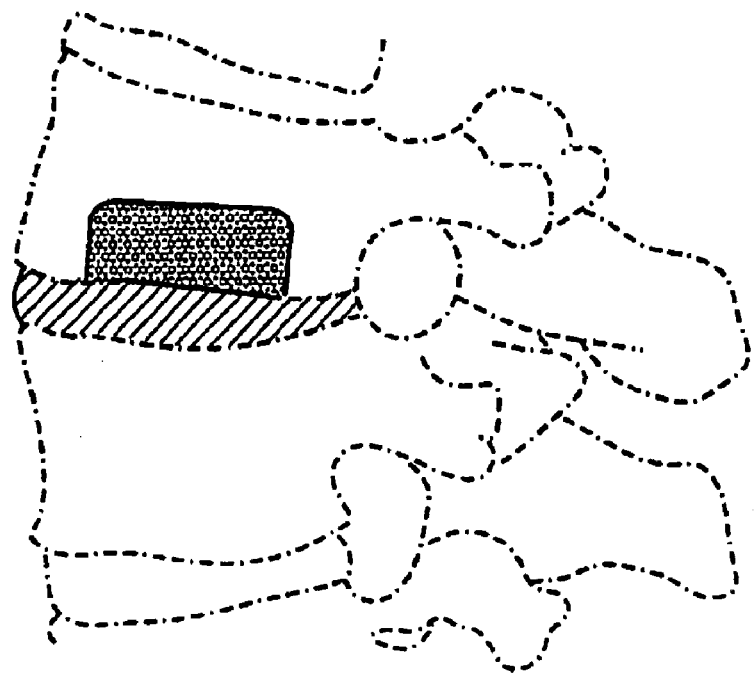
FIG. 11D is a view of the lateral surface of the spine drawn in FIG. 11A.

FIG. 11C is a coronal cross section of the spine drawn in FIG. 11B, after the insertion of an intradiscal device. FIG. 11D is a view of the lateral surface of the spine drawn in FIG. 11A. In this case the AF has not been cut.

Figure 12A:
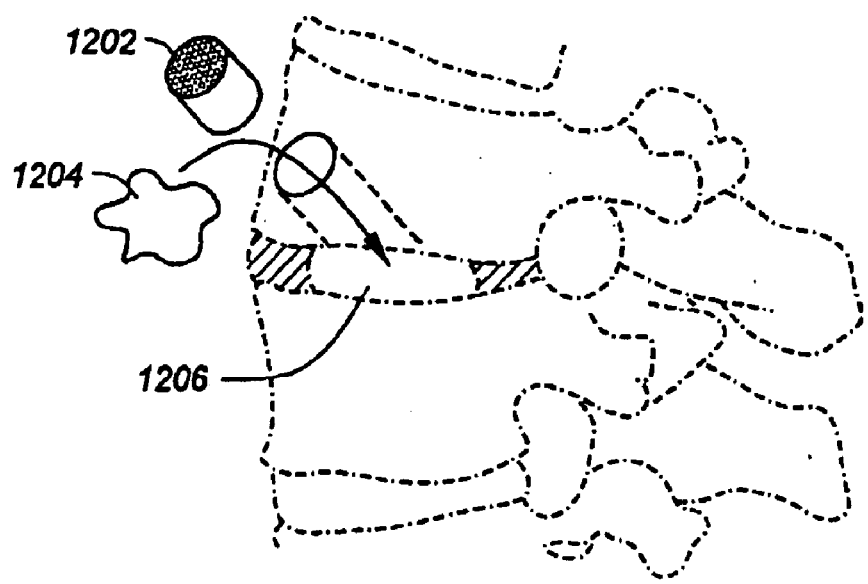
FIG. 12A is a drawing that shows an alternative approach according to the invention.
Figure 12B:
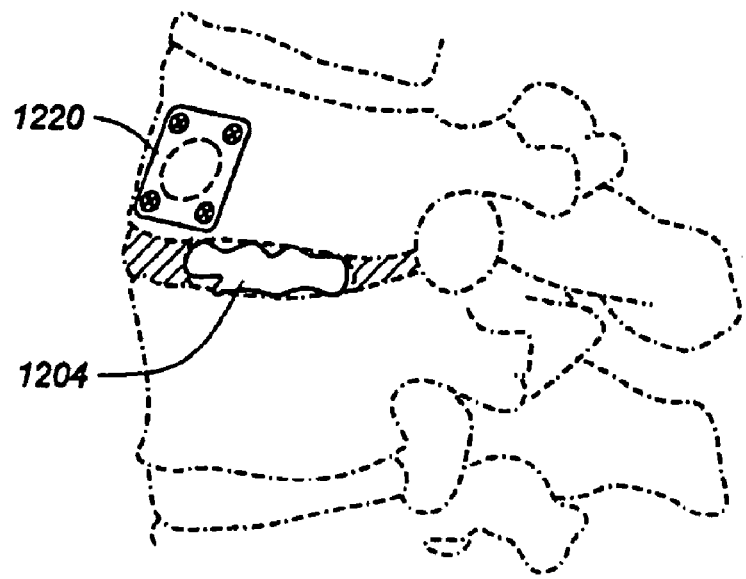
FIG. 12B shows the use of a plate and screws following the procedure of FIG. 12A.

FIG. 12A is a drawing that shows an alternative approach according to the invention, wherein a plug 1202 is removed from one of the vertebral bodies using a hole saw, for example, to gain access to the intradiscal space 1206 without having to cut the annulus. After some form of natural or synthetic disc augmentation or replacement material 1204 is inserted into the disc space, the plug 1202 or autograft/allograft may be inserted and optionally secured with a plate 1220 and screws. FIG. 12B shows the use of a plate and screws following the procedure of FIG. 12A.

I claim:

1. A method of placing an intradiscal device into an intradiscal space between upper and lower vertebral bodies, each body having a section on opposing sides of the intradiscal space, the method comprising the steps of:

truncating or removing at least a portion of the section of one or both of the upper and lower vertebral bodies;

inserting an intradiscal device into the intradiscal space; and reattaching the truncated or removed portion to the vertebral body.

2. The method of claim 1, further including the step of providing a device for securing the attached or reattached portion to the vertebral body.

3. The method of claim 2, further including the step of removing the device after the attached or reattached portion fuses to the vertebral body.

4. The method of claim 2, wherein the truncated or removed portion includes a part of an annulus fibrosis.

5. The method of claim 1, wherein:

a portion of both the upper and lower vertebral bodies are truncated or removed; and a dam material is used between the attachments.

6. The method of claim 5, wherein the dam material is flexible.

* * * * *